(12) United States Patent
Thery et al.

(10) Patent No.: US 12,139,740 B2
(45) Date of Patent: Nov. 12, 2024

(54) METHOD FOR DETERMINING THE INVASIVE POTENTIAL OF A TUMOR CELL

(71) Applicants: COMMISSARIAT A L'ENERGIE ATOMIQUE ET AUX ENERGIES ALTERNATIVES, Paris (FR); INSERM (INSTITUT NATIONAL DE LA SANTÉ ET DE LA RECHERCHE MÉDICALE), Paris (FR)

(72) Inventors: Manuel Thery, Paris (FR); Yoran Margaron, Voiron (FR); Odile Filhol-Cochet, Claix (FR)

(73) Assignees: COMMISSARIAT A L'ENERGIE ATOMIQUE ET AUX ENERGIES ALTERNATIVES, Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 1324 days.

(21) Appl. No.: 16/615,418

(22) PCT Filed: May 30, 2018

(86) PCT No.: PCT/EP2018/064129
§ 371 (c)(1),
(2) Date: Nov. 21, 2019

(87) PCT Pub. No.: WO2018/219980
PCT Pub. Date: Dec. 6, 2018

(65) Prior Publication Data
US 2020/0102590 A1     Apr. 2, 2020

(30) Foreign Application Priority Data

May 31, 2017   (EP) .................................... 17305633

(51) Int. Cl.
| | | |
|---|---|---|
| C12Q 1/02 | (2006.01) | |
| C12M 1/34 | (2006.01) | |
| C12N 5/09 | (2010.01) | |
| G01N 33/50 | (2006.01) | |

(52) U.S. Cl.
CPC ............... *C12Q 1/02* (2013.01); *C12M 41/46* (2013.01); *C12N 5/0693* (2013.01); *G01N 33/5011* (2013.01)

(58) Field of Classification Search
None
See application file for complete search history.

(56) References Cited

U.S. PATENT DOCUMENTS

| | | |
|---|---|---|
| 7,955,838 B2 | 6/2011 | Bornens et al. |
| 8,765,472 B2 | 7/2014 | Thery |
| 9,070,702 B2 | 6/2015 | Gabriel et al. |
| 9,250,241 B2 | 2/2016 | Thery et al. |
| 9,902,757 B2 | 2/2018 | Thery et al. |
| 10,711,248 B2 | 7/2020 | Fernandes et al. |
| 11,061,017 B2 | 7/2021 | Degot et al. |
| 2007/0042483 A1 | 2/2007 | Bornens et al. |
| 2013/0130394 A1 | 5/2013 | Thery et al. |
| 2014/0024041 A1 | 1/2014 | Tseng et al. |
| 2014/0024045 A1 | 1/2014 | Thery et al. |
| 2015/0048513 A1 | 2/2015 | Gabriel et al. |
| 2016/0312187 A1 | 10/2016 | Fernandes et al. |
| 2018/0356400 A1 | 12/2018 | Degot et al. |

FOREIGN PATENT DOCUMENTS

| | | |
|---|---|---|
| EP | 2 180 042 | 4/2010 |
| EP | 2 492 340 | 8/2012 |
| WO | WO 01/42786 | 6/2001 |
| WO | WO 2010/046459 | 4/2010 |
| WO | WO 2012/162345 | 11/2012 |
| WO | WO 2016/191532 | 12/2016 |

OTHER PUBLICATIONS

Burute, M. et al. "Polarity Reversal by Centrosome Repositioning Primes Cell Scattering during Epithelial-to-Mesenchymal Transition" *Developmental Cell*, Jan. 23, 2017, pp. 168-184, vol. 40, No. 2.

Tseng, Q. et al. "Study of multicellular architecture with controlled microenvironment—Thesis For the degree of Doctor of Philosophy" *Universite de Grenoble*, Sep. 12, 2011, pp. 1-213, retrieved from the Internet: http://tel.archives-ouvertes.fr/docs/00/62/22/64/PDF/24801_TSENG_2011_archivage_1_.pdf.

Written Opinion in International Application No. PCT/EP2018/064129, Jun. 20, 2018, pp. 1-10.

*Primary Examiner* — Thane Underdahl
(74) *Attorney, Agent, or Firm* — SALIWANCHIK, LLOYD & EISENSCHENK (57) ABSTRACT

The present invention relates to a method for predicting the invasive potential of a tumor cell and predicting the efficiency of a treatment. The method is based on the combination of at least three parameters, namely the internuclear distance, the polarization and the cell-cell connectivity.

14 Claims, 10 Drawing Sheets

| Name | BT-20 | | | Hs-578T | | | RPE1 | | | MDA-MB-157 | | | MDA-MB-231 | | | MDA-MB-436 | | | MDA-MB-468 | | | MCF0A | | | BT-549 | | | HCC38 | | | HCC70 | | | HCC1143 | | | HCC1937 | | |
|---|---|---|---|---|---|---|---|---|---|---|---|---|---|---|---|---|---|---|---|---|---|---|---|---|---|---|---|---|---|---|---|---|---|---|---|---|---|---|---|
| Replicate | 1 | 2 | 3 | 1 | 2 | 3 | 1 | 2 | 3 | 1 | 2 | 3 | 1 | 2 | 3 | 1 | 2 | 3 | 1 | 2 | 3 | 1 | 2 | 3 | 1 | 2 | 3 | 1 | 2 | 3 | 1 | 2 | 3 | 1 | 2 | 3 | 1 | 2 | 3 |
| Score | 1 | 3 | 3 | 2 | 2 | 2 | 1 | 1 | 2 | 3 | 4 | 3 | 4 | 3 | 4 | 4 | 4 | 4 | 2 | 1 | 2 | 1 | 1 | 1 | 3 | 3 | 3 | 2 | 1 | 2 | 2 | 2 | 2 | 2 | 2 | 2 | 2 | 3 | 3 |
| Score mean | 2 | | | 2 | | | 1 | | | 3 | | | 4 | | | 4 | | | 2 | | | 1 | | | 3 | | | 2 | | | 2 | | | 2 | | | 3 | | |

FIGURE 2D

| Low invasiveness | | High invasiveness | |
|---|---|---|---|
| Very low | Low | Intermediate | High |
| MCF10A<br>RPE1 | HCC1143<br>Hs578T<br>MDA-MB-468<br>HCC38<br>HCC70 | BT-549<br>MDA-MB-157<br>BT-20<br>HCC1937 | MDA-MB-231<br>MDA-MB-436 |

| Low invasiveness | High invasiveness | |
|---|---|---|
| Low | Intermediate | High |
| MCF10A<br>BT-20<br>HCC38<br>HCC1143<br>MDA-MB-468 | BT-549<br>Hs578T<br>HCC70<br>HCC1937 | RPE1<br>MDA-MB-157<br>MDA-MB-231<br>MDA-MB-436 |

METHOD FOR DETERMINING THE INVASIVE POTENTIAL OF A TUMOR CELL

CROSS-REFERENCE TO RELATED APPLICATION

This application is the U.S. national stage application of International Patent Application No. PCT/EP2018/064129, filed May 30, 2018.

FIELD OF THE INVENTION

The invention relates to the field of medicine, in particular oncology. More particularly, it relates to a method for classifying tumors in term of invasiveness.

BACKGROUND OF THE INVENTION

Cancer invasion is a pathophysiological process occurring locally from a primary neoplastic tissue to metastasis dissemination within distant organs.

Cancer diagnosis from a tumor is actually mainly achieved from the histological examination of tumor biopsies. Based on qualitative estimations of the sample composition (cells and nuclei morphology, mitosis frequency), clinicians can classify tumors in tree grades by using the Nottingham Histologic Score system, also known as the Elston-Ellis modification of Scarff-Bloom-Richardson grading system (Elston C W et al. (1991). Histopathology. 19:403-410) or the WHO/IARC classification (Lantuejoul S et al. (2016). Ann Pathol. 36:5-14). Based on such a classification, these methods are used to estimate cancer invasiveness and are crucial to choose the best treatment options. However, because these methods are based on subjective and qualitative estimations of histological features from damaged tissue samples due to surgery, they fail in robustly quantify tumor-derived cell features and subsequently in accurately classifying tumors for their invasive potential.

Invading tumor cells initially encompass a deep reorganization of their overall morphology as their intracellular organization, including a reorientation of their polarity. Indeed, defect in the cell's ability to adapt its internal polarity to external cues is a hallmark of cancer (Wodarz A et al. (2007). Nat Cell Biol. 9:1016-1024; Lee M, et al. (2008). J Cell Sci. 121:1141-1150) and regulators of cell polarity can act as tumor suppressors (Royer C, et al. (2011). Cell Death Differ. 18(9):1470-1477). A major program of molecular events triggering cell invasion from a stationary state is called epithelial-to-mesenchymal transition (EMT). This multistep process (1) involves the reversal of epithelial polarity, (2) a partial to full cell individualization, and (3) a cell scattering to the surrounding tissue initiating invasion (Yeung K T, et al. (2017). Mol Oncol. 11:28-39). In a recent study, Théry and colleagues demonstrate that polarity reversal is a key event of EMT (Burute M, et al. (2017). Dev Cell. 40, 168-184).

As a prerequisite of cell polarity, the asymmetry of internal cell organization is conferred by the anisotropic distribution of microtubules, which beam from a nucleation organelle: the centrosome (Bornens M, (2008). Nat Rev Mol Cell Biol. 9:874-886). Depicted as the main microtubule organizing center, the centrosome adopts an eccentric positioning highly relevant to the internal cell polarity. As a hallmark of cell polarity, the centrosome is associated with more than a hundred of regulatory proteins that make it a spatial organizer of organelle positioning and signaling pathways (Doxsey S, et al. (2005). Annu Rev Cell Dev Biol. 21:411-434). Notably in epithelial cells, the centrosome is located close to cell-cell junction at the apical pole, but after cell dissociation and plating on Petri dishes, the unlimited surface classically used for the culture of adherent mammalian cells, this positioning is disrupted. This suggests that classical culture of adherent cells on unlimited adhesive surface fails to capture this important feature of centrosome positioning regulation and subsequently is not suitable for revealing the subtle changes occurring during the initiation of tumor invasion.

In order to promote adhesion of cells in a specific and determined position, EP1664266 and EP2180042 disclose a culture device comprising an adhesive surface, named adhesive micropatterns, having a determined shape onto which cells can adhere. These patent applications also disclose a method for controlling cell shape and internal organization, and the use of such a device for screening biologically active compounds. In such a device, once cells are attached to such surface, they use the adhesive clues provided to adopt the overall shape of the surface while cell's organelles are disposed in a controlled organization. Cells may then be normalized from their spatial configuration that adopts the geometry of the adhesive surface.

By recapitulating advanced mechanical cues involved in epithelial cell polarity initiation and maintenance, recent breakthrough made by the group of M. Théry disclose a minimal epithelium model composed of MCF10A cell doublets cultured on H micropatterns, which fully mirrors the in vivo phenotype of centrosome in term of positioning (Burute M, et al. (2017). Dev Cell. 40, 168-184). This study shows that MCF10A cell cultured on H micropatterns during 24 hours divide and the obtained cell doublet adopt a standardized shape with a highly normalized internal organization: the centrosome is found off-centered, close to the intercellular junction; and the nucleus-centrosome axis is oriented toward this junction. After centrosome and nucleus staining using pericentrin antibody and Hoechst respectively, automated image acquisitions and processing, the quantification of cell polarity descriptors shows very robust results segregating polarized cells to the junction (72% in MCF10A). The addition of an EMT inducer, TGF-beta, largely lowers polarized MCF10A cells to 32%, provokes a switch in polarity index and increases internuclear and intercentrosomal distances. Although the disclosed descriptors are efficient to detect EMT within healthy cell types, in a black and white manner, the focus of this study is not devoted to assess tumor invasion. Moreover, the method employed in Burute M, et al is not suited for finely comparing cancer cells of gradual invasiveness, as will be illustrated in the example section.

Tumor diagnosis is actually subjective. Indeed, because histological examination is based on subjective and qualitative estimations of features from damaged tissue samples due to surgery, it fails in robustly quantifying tumor-derived cell features and subsequently in accurately classifying tumors for their invasive potential. In addition, tumor diagnosis is not directly associated with therapeutic options. Therefore, there is still a strong need for a method for classifying tumors in term of their invasive potential, especially for prognosis and as a companion test to predict efficient pharmacopeia in personalized medicine.

SUMMARY OF THE INVENTION

The invention relates to a method for classifying tumors in term of invasiveness and drug response.

The method based on such classification can be useful for cancer diagnosis stating the invasive potential of tumor cells and outlining prognosis, and can be used as a companion test dedicated to personalized medicine predicting anti-tumor effects from molecules lowering tumor invasion or growth.

Accordingly, the present invention relates to a method for predicting the invasive potential of a tumor cell, comprising:
providing a culture device comprising a plane substrate and at least two sets of two adhesive patterns for culturing adherent cells on said substrate,
wherein the two adhesive patterns are sufficiently separated from each other by an essentially non-adhesive intercalating area for preventing a cell on a first adhesive pattern to reach another adhesive pattern; and, the area covered by the two adhesive patterns and the intercalating area is sufficient to adhere two animal cells, and wherein each set of two adhesive patterns is isolated by a cytophobic surrounding region;
seeding at least one tumor cell on said sets of two adhesive patterns;
culturing said tumor cell so as to obtain one cell doublet from one cell division on said sets of two adhesive patterns;
measuring at least the following three parameters on said sets of two adhesive patterns for said tumor cell:
the internuclear distance for each set of two adhesive patterns;
the cell-cell connectivity for each set of two adhesive patterns; and
the percentage of highly polarized cells to the total cell population on said sets of two adhesive patterns;
determining the tumor cell invasive potential based on the at least three measured parameters.

Preferably, the distance between the two adhesive patterns is comprised between about 2/3 D and about 4/3 D, D being the diameter of the surface S covered by the cell on a support without any constraint, and the area covered by the adhesive pattern for each cell is less than 80% of the cell surface S covered by the cell on a support without any constraint. In particular, the set of two adhesive patterns has the form of a H.

Preferably, the highly polarized cells are cells having a centrosome located in close proximity of the cell-cell junction, in a triangular area defined as:

$$|y| \leq (x-0.5)*\tan 60$$

with $0.5 \leq x \leq 2$ wherein x is the position of the centrosome on a nucleus-nucleus axis pointing toward the intercellular junction and y is the position of the centrosome on an axis perpendicular to the nucleus-nucleus axis, the unit being the radius of the nucleus.

Preferably, the cell-cell connectivity is the difference between the area of the convex envelope surrounding the cell doublet and the area of the cell doublet.

Preferably, in addition to the tested tumor cell, cells of reference with predetermined invasive potential are seeded on the device, cultured and the parameters are measured. In particular, said cells of reference are selected from the group consisting of a cell with very low or no invasive potential, a cell with low invasive potential, a cell with intermediate invasive potential, a cell with high invasive potential and a cell with very high invasive potential.

Preferably, the invasive potential of the tumor cell is determined by comparison with cells of reference. In particular, a statistical analysis is carried out in order to determine the cells of reference which have the highest similarity with the tested tumor cell. More preferably, the statistical analysis is carried out by principal component analysis.

The present invention also relates to a method for providing information useful for diagnostic or prognosis of a subject comprising performing the method for predicting the invasive potential of a tumor cell according to the present invention.

The present invention further relates to a method for assessing the efficiency of a molecule for the treatment of a tumor in a subject comprising contacting the molecule with a tumor cell from the tumor of the subject, determining the invasive potential of the tumor cell treated with the molecule, comparing the determined invasive potential of the tumor cell treated with the molecule with the invasive potential of the untreated tumor cell and selecting the molecule if the invasive potential is decreased, wherein the invasive potential of the tumor cell is determined by the method for predicting the invasive potential of a tumor cell according to the present invention.

Preferably, the tumor is a solid tumor. In particular, the solid tumor is a carcinoma. Preferably, the tumor is selected from the group consisting of breast cancer, colorectal cancer, lung cancer, kidney cancer, thyroid cancer, prostate cancer, liver cancer, pancreas cancer, head and neck cancer, and ovaries cancer, preferably from breast, colon, lung, kidney and thyroid cancer.

DETAILED DESCRIPTION OF THE INVENTION

The invention provides a method to accurately classify a tumor for its invasive potential. This method is based on the combination of three parameters which are necessary and sufficient to classify a tumor for its invasive potential. The three essential parameters are the internuclear distance, the cell-cell connectivity and the percentage of highly polarized cells to the total cell population on several sets of two adhesive patterns. Of course, additional parameters can be combined with these three essential parameters.

One advantage of the invention is that results from this classification not only tallies a tumor physiopathology for diagnosis, but also provides a prediction of a potential malignancy degree and subsequently a prognosis for the patient.

Another advantage of the invention is that the classification method enables an extrapolation from the efficiency of a compound to affect the behavior of cells cultured from a tumor, to curative or palliative efficiency of said compound to treat this particular tumor.

Accordingly, the present invention relates to a method for predicting the invasive potential of a tumor cell, comprising:
providing a culture device comprising sets of two adhesive patterns for culturing adherent cells on said substrate,
seeding at least one tumor cell on said sets of two adhesive patterns;
culturing said tumor cell so as to obtain one cell doublet from one cell division on said sets of two adhesive patterns;
measuring the following three parameters on said sets of two adhesive patterns:
the internuclear distance for each set of two adhesive patterns;
the cell-cell connectivity for each set of two adhesive patterns; and
the percentage of highly polarized cells to the total cell population on said sets of two adhesive patterns;

determining the tumor cell invasiveness based on the three measured parameters.

Culture Device

The culture device is a device as disclosed in the patent application WO2010/046459. In particular, it comprises sets of adhesive patterns with specific geometries preventing the rotating movement of cells and conferring them spatial adhesive conditions allowing achievement of a mechanical equilibrium and a stationary and reproducible conformation. WO2010/046459 provides the rules allowing the design of a device for adhering two cells in a multicellular arrangement with a mechanically stable and reproducible conformation. The rules are the followings: one adhesive pattern for each cell of the multicellular arrangement. The zone between the two adhesive patterns has been called intercalating area. The adhesive patterns are sufficiently separated from each other by an essentially non-adhesive intercalating area for preventing a cell on a first adhesive pattern to reach another adhesive pattern. Of course, the adhesive patterns have also to be sufficiently near to allow the interaction between the cells. It has been established that the intercalating area is about one diameter of the cell's surface (D). The adhesives patterns are preferably less than the surface area of the cell (S). These small adhesive patterns are important as they provide the cells with a sufficient freedom degree (by the non-adhesive area) to allow them wedging one against each other. The equilibrium between those two constraints (the adhesive pattern and the other interacting cell) stabilizes the interacting cells and allows them to adopt a natural position, therefore stable and reproducible. In order to provide sufficient freedom degree to the cells, the intercalating area is essentially non-adhesive. However, the intercalating area may include adhesive area, more preferably a single adhesive area, thereby helping the cells to meet each other and establish the interaction contact. The width of this adhesive area of the intercalating zone has to be narrow (less than 1/2 cell's diameter). Indeed, if this area is too large, it can allow the cell reaching the other adhesive pattern. The area of the two adhesive patterns with the intercalating area is sufficient to adhere two animal cells. Of course, in order to avoid the disturbance of the multicellular arrangement by surrounding cells (not involved in the multicellular arrangement), each set of patterns is surrounded by a cytophobic region.

The device of the present invention comprises a plate defining a surface, and at least two sets of two adhesive patterns being sufficiently separated from each other by an essentially non-adhesive intercalating area for preventing a cell on a first adhesive pattern to reach another adhesive pattern and the area of the two adhesive patterns with the intercalating area is sufficient to adhere two animal cells. In other words, the area covered by the two adhesive patterns and the intercalating area is sufficient to adhere two animal cells and each cell adheres to one individual adhesive pattern. In particular, the plate defines a plane surface. In particular, the area covered by the two adhesive patterns and the intercalating area is too large for being covered by a single cell. Accordingly, this area is far more than 1 S. For instance, for a multicellular arrangement of 2 cells, this area will be about 2 S.

The area defined by the convex envelope of each adhesive pattern is comprised between about 1/2 S and about 3/2 S, S being the area covered by a cell without any constraint. In a preferred embodiment, the area defined by the convex envelope of each adhesive pattern is comprised between about 3/4 S and about 5/4 S, more preferably about S. For instance, S can be comprised between 1 and 2,500 $\mu m^2$, more preferably between 1 and 1,000 $\mu m^2$, still more preferably between 1 and 500 $\mu m^2$ or 500 to 900 $\mu m^2$. S may depend on the cell type. However, the area defined by the convex envelope of each adhesive pattern includes a high percentage of non-adhesive area, for instance at least 20, 30, 40 or 50%, preferably between 20-70%, 30-60%, or 40-50% of non-adhesive area. Alternatively, the area covered by the adhesive pattern for each cell is less than 80, 70, 60 or 50% of the cell surface S. For instance, the area of each adhesive pattern is between 30-80%, 40-70% or 50-60% of the cell surface S. This area could also be defined as the surface covered by one cell once the mechanical equilibrium is reached.

The convex envelope of each adhesive pattern can have any kind of form (e.g., disk, square, rectangle, trapezoid, disk fragment, ellipse, etc.). On this convex envelope, it can be defined a long axis and a short axis.

The adhesive pattern can be formed of single connected adhesive surfaces and/or of several non-connected adhesive surfaces. By "single connected adhesive surface" is preferably intended a solid line or curve. By "non-connected adhesive surfaces" is preferably intended dotted or dashed line or curve, or discrete point or area. In a preferred embodiment, the adhesive pattern consists of a combination of adhesive elements selected from a line, a curve and a point. The width of the adhesive point, lines, curves or edges is preferably between 0.1 to 100 µm, more preferably between 1 to 50 µm, still more preferably about 8 µm.

In a preferred embodiment, the distance between two adhesive patterns within a set is comprised between about 2/3 D and about 4/3 D. In a preferred embodiment, the two adhesive patterns within a set are separated by a distance of between about 3/4 D to about 5/4 D, more preferably about D.

In a preferred embodiment, the essentially non-adhesive intercalating area comprises a single adhesive zone. The single adhesive zone is suitable for not allowing a cell to reach another adhesive pattern. That is to say that this single adhesive zone has to be narrow. Indeed, a long and fine adhesive line parallel to the large axis of the adhesive pattern is not appropriate because it can allow the cell to reach another adhesive pattern. For instance, the adhesive zone is a zone located between two adhesive patterns of a set and having a width of less than D, preferably less than 1/2 D, preferably less than 1/3 D, more preferably less than 1/4 D. In one embodiment, the adhesive zone can connect two adhesive patterns, for instance as a line or a curve. In another embodiment, the adhesive zone can be between the two adhesive patterns without any connection with them. While not wishing to be bound by theory, it is thought that this adhesive zone helps the two cells to establish the cell-cell interaction. In a preferred embodiment, 50% of the essentially non-adhesive intercalating area is non-adhesive, more preferably 60, 75, 80, 85 or 90%. The single adhesive zone can be comprised of a single connected adhesive surface and/or of several non-connected adhesive surfaces forming the adhesive zone.

In a most preferred embodiment, the device of the invention is such that the distance between two adhesive patterns of a set is comprised between about 2/3 D and about 4/3 D, preferably between about 3/4 D to about 5/4 D, more preferably about D; the essentially non-adhesive intercalating area comprises a single adhesive zone, said single adhesive zone being located between two adhesive patterns and having a width of less than D, preferably less than 1/2 D, preferably less than 1/3 D, more preferably less than 1/4

D; and, the area covered by the adhesive pattern for each cell is less than 80, 70, 60 or 50% of the cell surface S.

In a particular embodiment, a set of two adhesive patterns can adopt the following forms: C, X, H, Z and II. In a most preferred embodiment, the set of two adhesive patterns has the form of a H.

Preferably, said device comprises a plurality of sets of two adhesive patterns isolated from each other by cytophobic regions to which cells do not adhere. More particularly, said device comprise at least 2 sets of two adhesive patterns, preferably at least 5, 10, 100, 1 000, 10 000, or 100 000 sets of two adhesive patterns. In a preferred embodiment, said device comprises between 5 and 25 000 sets of two adhesive patterns/cm$^2$, more preferably between 5000 and 10000 sets of two adhesive patterns/cm$^2$, still more preferably about 7500 sets of two adhesive patterns/cm$^2$.

The adhesive pattern or zone comprises molecules that promote cell attachment. These molecules can be non-specific like oxidized polystyrene like in tissue culture treated polystyrene dish. The molecules can also be specific adhesion molecules such as the one that are well known to those of ordinary skilled in the art and comprise antigens, antibodies, cell adhesion molecules, extracellular matrix molecules such as type I collagen, type IV collagen, laminin, fibronectin, synthetic peptides, carbohydrates and the like. Preferably, said adhesive patterns comprise extracellular matrix molecules, more preferably fibronectin.

The non-adhesive surface is an inert surface. An appropriate inert surface is a surface covered by a derivative of poly(ethylene glycol).

The plate is a support convenient for confocal, optical and/or fluorescence microscopies. In the more preferred embodiment, the plate is glass, possibly covered with a thin layer of oxidized polystyrene. For example, a convenient plate according to the present invention is a coverslip or a slide. The support can also be a plastic modified for cell culture. It can also be a thermoformed plastic plate or a tissue culture treated Petri dish. It is understood in the present invention that the plate preferably refers to a plane surface without any well. Alternatively, the plate can be a soft substance having a Young's modulus comprises between 5 and 100 kPa.

The device according to the present invention can comprise several groups of a set of adhesive patterns on the same plate separated from each other such that each group can be incubated in a different medium. For instance, a group of a set of adhesive patterns can be contacted with a test compound and another group can be contacted with another test compound or without any test compound. This separation can be provided by a physical barrier such as teflon seal. For example, see SPI Teflon® of SPI Supplies, Teflon® Printed Slides of Aname.

The device according to the present invention with adhesive patterns and zones, and the cytophobic regions are formed by micropatterning. Microcontact printing or UV patterning can be used. Standard methods are well known by those skilled in the art. For review, see Whitesides et al (Annu. Rev. Biomed. Eng., 2001, p. 335-373, more particularly p. 341-345).

Tumor Cells

The tested tumor cells can be any tumor cell. Preferably, the tumor cells can be obtained from a subject having a tumor. The tumor cells can be obtained from a biological sample of the subject containing tumor cells. Examples of such a biological sample include biopsies, organs, tissues or cell samples. Preferably, the biological sample is a biopsy sample.

The subject is preferably a mammal. It can be a human being or an animal. The animal can be a pet.

For instance, the subject can be dogs, cats, horses, cows, pigs, sheep and non-human primates, among others.

Any kind of tumor cell can be used in the present invention. Cells can be for example fibroblast, endothelial and epithelial cell. In a preferred embodiment, the cells are epithelial cells.

For instance, the tumor cell can be from a solid or hematopoietic tumor. Preferably, the tumor cell is from a solid tumor. Examples of solid tumors are sarcomas, carcinomas, and lymphomas. In a preferred embodiment, the solid tumor is a carcinoma.

The tumor can be selected from the group consisting of breast cancer, colorectal cancer, lung cancer, kidney cancer, thyroid cancer, prostate cancer, liver cancer, pancreas cancer, head and neck cancer, and ovaries cancer, preferably from breast, colon, lung, kidney and thyroid cancer.

Accordingly, the method may comprise a previous step of providing a tumor cell from the subject.

Cells of Reference

In addition to the tumor cells to be tested, cells of reference can be used in parallel on the culture device.

The cells of reference are cells for which the invasive potential has been previously established/determined. These cells are used to determine the level for the invasiveness. For instance, one first cell of reference may have a low invasive potential and one second cell of reference may have a high invasive potential. Optionally, several cells of reference can be used such as cells selected from the group consisting of a cell with very low or no invasive potential, a cell with low invasive potential, a cell with intermediate invasive potential, a cell with high invasive potential and a cell with very high invasive potential. In a preferred embodiment, at least four cells of reference are used in the method: a cell with very low or no invasive potential, a cell with low invasive potential, a cell with intermediate invasive potential, a cell with high or very high invasive potential.

For instance, cells with no or very low invasive potential can be a non-tumor cell (e.g., MCF10A or RPE1). Cells with low invasive potential can be for instance HCC1143, Hs578T, MDA-MB-468, HCC38, HCC70). Cells with intermediate invasive potential can be for instance BT-549, MDA-MB-157, BT-20, HCC1937). Cells with high invasive potential could be MDA-MB-231 or MDA-MB-436. In particular, MDA-MB-231 cell line is known as extremely invasive cells.

The invasive potential of cells of reference can be determined by any method and classification available to the person skilled in the art. The invasive potential can be determined according to the Nottingham Histologic Score system (the Elston-Ellis modification of Scarff-Bloom-Richardson grading system) or the WHO/IARC classification. Invasive potential means the ability of cells to invade neighboring or distant tissues. The motility of cells can be measured according to, for example, the gold colloid method. The gold colloid method is a method wherein cells are seeded onto a cover glass with colloidal gold adhering thereto, and the area of the gold-lacking portion formed on the motion track thereof is calculated, whereby the motility of the cells is measured. The motility and invasive potential of cells can be evaluated by Boyden chamber assay and the like. In Boyden chamber assay, the motility is first evaluated by the number of cells that have passed an uncoated porous PET membrane, then using a PET membrane coated with a basal membrane, the number of cells that have degraded the basal membrane, passed the pores, and migrated to below the membrane is measured, and the ratio to the number of cells that have migrated is measured, whereby the invasive potential of the cells is evaluated.

Alternatively, the invasive potential of cells can be measured by time-lapse microscopy of migrating cells on 2D or 3D matrixes, scratch/wound healing assay or soft agar invasion assay.

Culturing, Fixation, Staining and Image Acquisition and Processing

The method comprises a step of seeding at least one tumor cell on said sets of two adhesive patterns and a step of culturing said tumor cell so as to obtain one cell doublet from one cell division on said sets of two adhesive patterns. More particularly, the tumor cell is cultured on the device for a period of time sufficient to allow the tumor cell to divide into two cells on said set of adhesive patterns, to adhere to each said adhesive pattern and to reach a mechanical equilibrium. The period of time may depend on the tumor cells and is well-known to the person skilled in the art. This incubation time is typically comprised between 1 and 2 days. Generally, a period of 24 h is sufficient.

In a preferred embodiment, several cells of reference with different level of invasive potential are also seeded and cultured on the culture device simultaneously with the cell tumor to be tested.

For instance, cells can be seeded at a density of 10,000 to 100,000 cells per $mm^2$ of chip, for instance about 25,000 cells per $mm^2$ of chip. The method may comprise a rinsing step in order to remove the non-attached cells.

At the end of this incubation time, cells can be fixed by any method known in the art, for instance by using cold methanol. Then, the cells are stained in order to visualize the centrosomes and nuclei. For instance, the centrosomes are immunostained with antibody directed against centrin, pericentrin, gamma-tubulin, ninein, Cep164, Cep192, Odf1, cenexin, centriolin and/or PLK4, preferably pericentrin. For instance, the nuclei can be stained by Hoechst labeling or DAPI (4',6-diamidino-2-phenylindole). Then, images of cells on the set of two adhesive patterns are acquired with any suitable microscope. The image acquisition can be automatically achieved.

Image analysis monitors the internal organization of cells from a doublet. It preferably comprises nucleus and centrosome binarization, computation of the center of mass of said nucleus and centrosome, computation of the length and orientations of the nucleus-nucleus vector of said doublet and the nucleus-centrosome vector within individual cells of said doublet, as well as the area of whole cell doublet and of it convex envelope.

In a preferred embodiment, the image processing includes the individualization of the set of two adhesive patterns, e.g. using a template matching method; the detection of nucleus and centrosome, e.g. based on thresholding and size filtering, within each cell of the doublets; for each doublet, the coordinates of the centrosomes and the nuclei center of mass are computed, as well as the area of whole cell doublet and of it convex envelope.

In a preferred embodiment, at least 50 cell doublets per type of cells are necessary for the analysis. However, the method may complete to use 50 to one thousand cell doublets per type of cells, preferably about 100 cell doublets.

Then, the three parameters necessary and sufficient to classify a tumor cell for its invasive potential are measured, namely the internuclear distance, the cell-cell connectivity and the percentage of highly polarized cells to the total cell population. These parameters are measured for the tumor cell to be tested and for cells of reference.

Internuclear Distance

The internuclear distance is the length between the nucleus of two cells on the set of two adhesive patterns. More particularly, the internuclear distance is the length between the nuclei center of mass of the two cells of the doublet.

Cell-Cell Connectivity

Figure 1A:
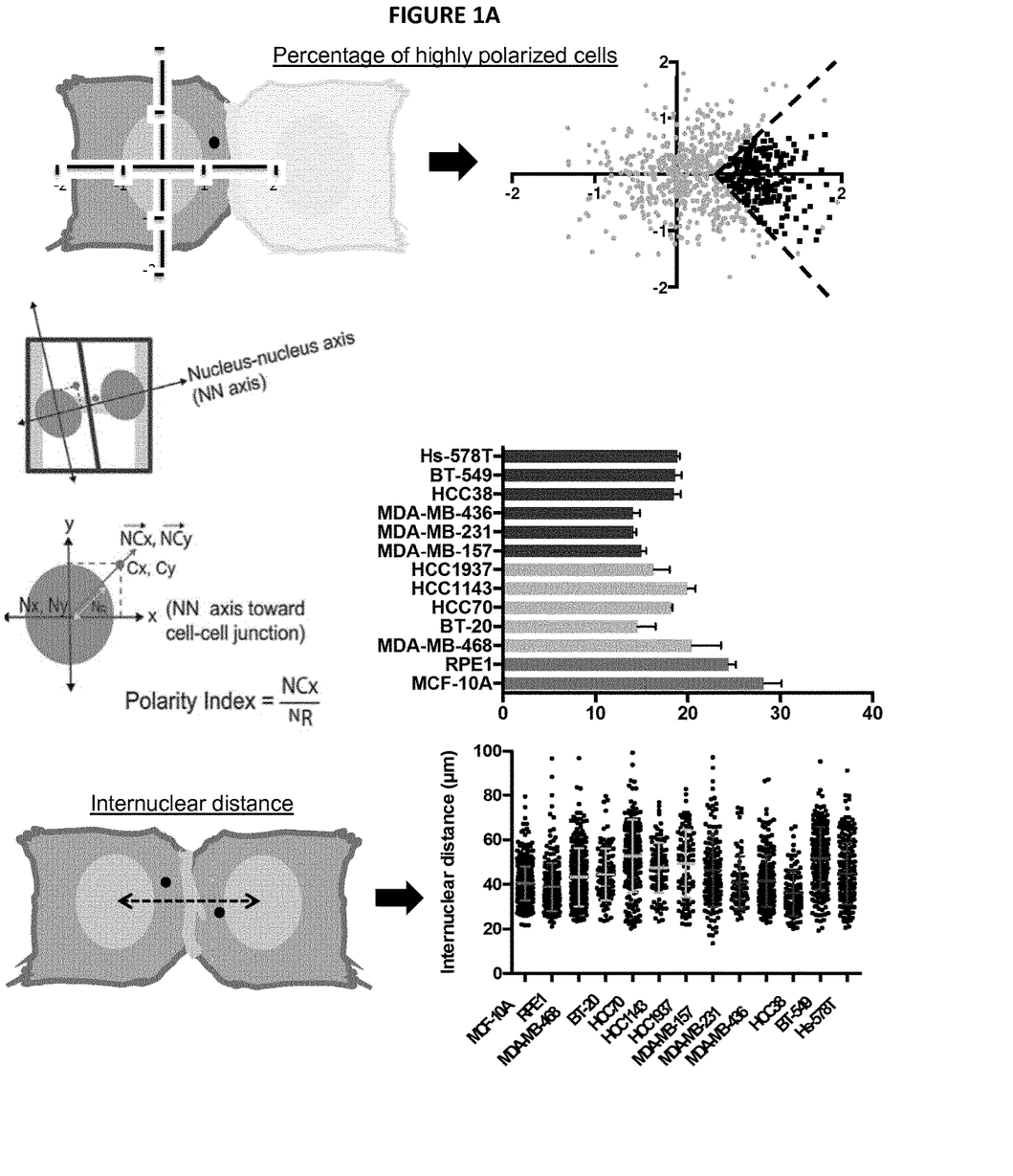

The cell-cell connectivity is defined as the difference between the area of the convex envelope surrounding the cell doublet and the area of the cell doublet. The cell-cell connectivity is illustrated in FIG. 1A. The dashed line is the convex envelope surrounding the cell doublet. The grey line defines the area of the cell doublet and the hashed area is the difference between the area of the convex envelope surrounding the cell doublet and the area of the cell doublet. The mean area of a cell doublet is generally of 1100 $\mu m^2$.

Percentage of Highly Polarized Cells

The cell polarization is determined on the basis of the position of centrosomes with respect to the nucleus-nucleus axis and a perpendicular axis as shown in FIG. 1A. Preferably, nucleus-centrosome vector orientations are measured with respect to the nucleus-nucleus axis pointing toward the intercellular junction. Nucleus-centrosome distances are normalized with respect to nucleus radius. Thus, positive coordinates corresponded to nucleus-centrosome axes pointing toward adjacent cells and large values to highly eccentric centrosome positions.

The highly polarized cells are quantified as the relative coordinates of the centrosome from its nucleus in the nucleus-nucleus axis of reference where the maximum radius of the nucleus is the arbitrary unit.

Highly polarized cells are then defined as cells having a centrosome located in close proximity of the cell-cell junction, in a triangular area defined as:

$$|y| \leq (x-0.5)*\tan 60$$

with $0.5 \leq x \leq 2$ wherein x is the position of the centrosome on a nucleus-nucleus axis pointing toward the intercellular junction and y is the position of the centrosome on an axis perpendicular to the nucleus-nucleus axis, the unit being arbitrary the radius of the nucleus. Accordingly, 1 corresponds to the length of the radius of the nucleus of the cell.

For instance, in FIG. 1A, the dashed lines define the area corresponding to the highly polarized cells. The percentage of highly polarized cells to the total cell population is the number of cells having a high polarization as defined above by the total number of cells tested for each kind of cells (e.g., tested tumor cell, cells of reference). More particularly, it is the ratio of the number of cells having a high polarization as defined above by the total number of cells*100.

The percentage of highly polarized cells illustrates the proportion of cells in a tumor having a weak invasive capacity. It is inversely correlated to the invasive potential of the tumor.

Additional Descriptors

Additional descriptors or parameters can further be taken into account for determining the invasive potential of a cell tumor. For instance, such additional parameters can be selected in the group consisting of the nucleus-centrosome distance, the nucleus diameter, the ratio between the nucleus-centrosome distance and the nucleus diameter, the area of the cell doublet, the angle between the nucleus-centrosome and the nucleus-nucleus axis, the solidity of the cell doublet (the ratio of the convex envelope to the area of the cell doublet), the coefficient of variability of the solidity of the cell doublet, the centrosome-centrosome distance within a cell doublet, the polarity index (in particular as defined in Burute et al, 2017; see also FIG. 1A), and the percentage of cells having a full polarity reversal to the total population.

Determining the Invasiveness

Based on the at least three parameters, the invasive potential of the tested tumor cell can be determined, in particular by comparison with cells of reference with a predetermined invasive potential.

Figure 1B:
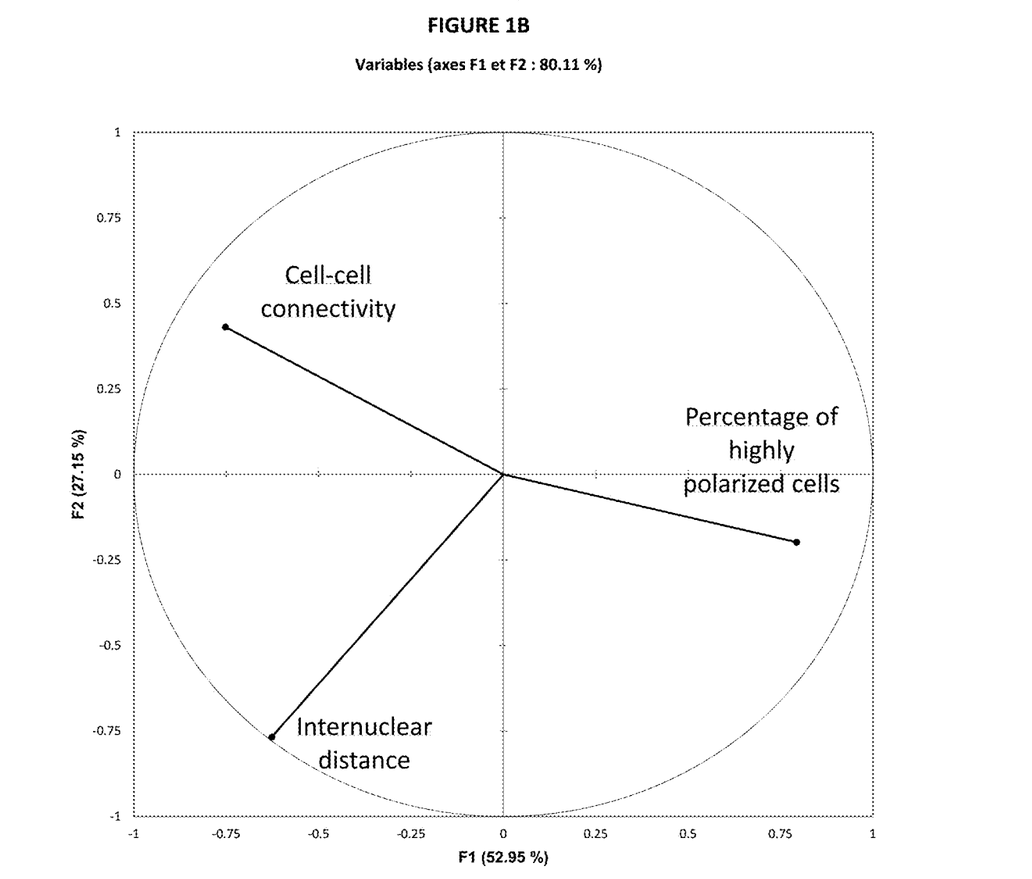
Figure 2A:
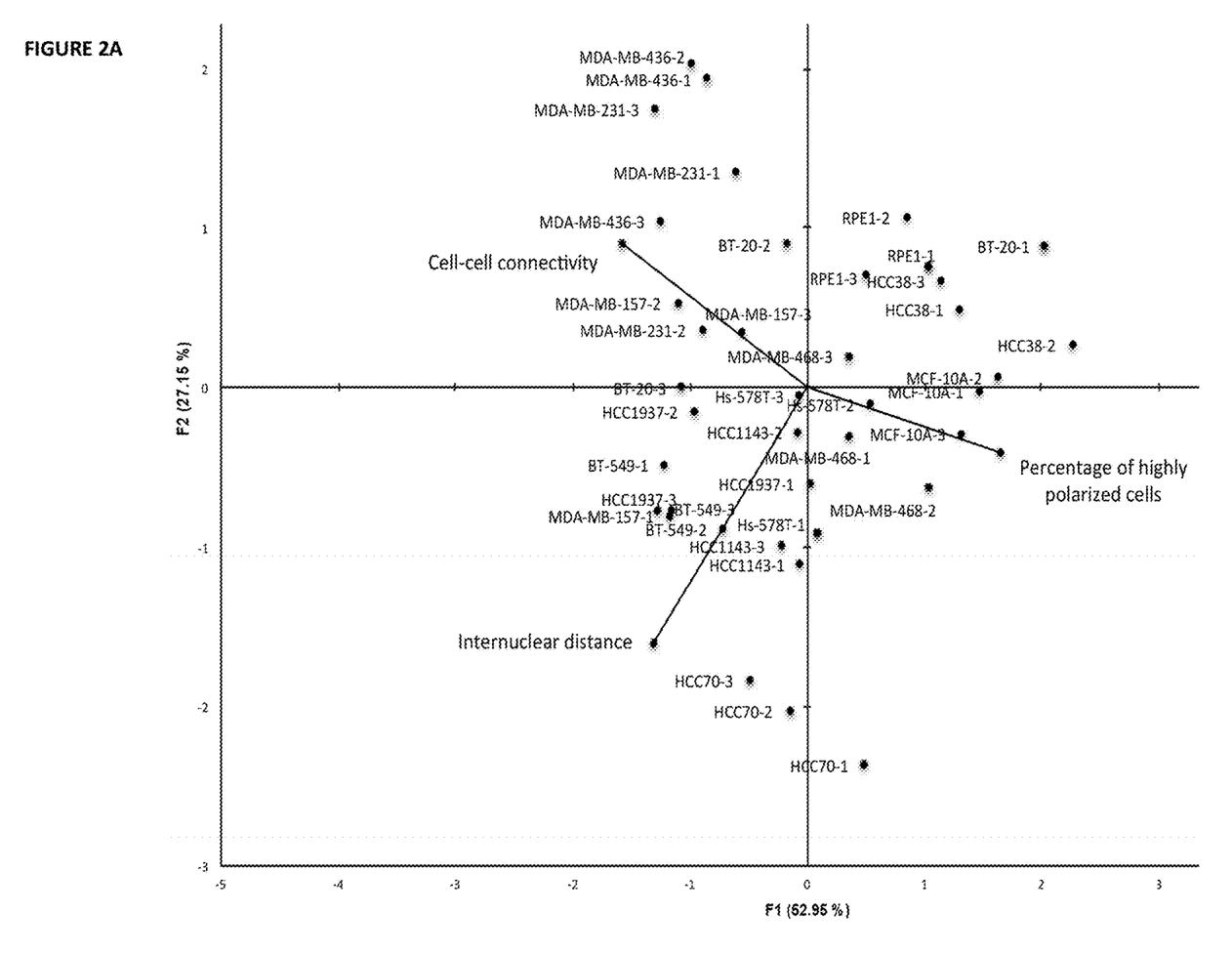

In a first aspect, each cell can be individually plotted in the eigenvector representation based on the at least three parameters, as indicated in FIGS. 1B and 2A.

In a second aspect, a statistical analysis is carried out in order to determine the cells of reference which have the highest similarity with the tested tumor cell. Preferably, the statistical analysis is carried out by a principal component analysis. In this analysis, each parameter or descriptor may be weighted in order to adjust their importance.

The statistical analysis allows the determination of a score. The statistical analysis leads to a classification in different categories of invasive potential. In a particular embodiment, the method allows the classification of the tumor cell into one of four categories, the categories being 1) no or very low invasive potential, 2) low invasive potential, 3) intermediate invasive potential, and 4) high invasive potential.

Use for Diagnosis

The determination of the invasive potential of cell tumors can be useful for diagnosis purpose, in particular in the oncology field. Therefore, the method according to the present invention can be used for diagnosis or prognosis purpose. In particular, it can be used for classifying the tumor of a subject.

Use for Predicting Drug Efficiency

The method according to the present invention can be used for assessing the efficiency of a molecule for the treatment of a tumor in a subject. Indeed, it can be used to measure the capacity of a molecule to decrease the invasive potential of a tumor cell. By a molecule is also considered a combination of different molecules.

Then, when the method is carried out for assessing the efficiency of a molecule to modify the invasive potential of a tumor cell, the tumor cell may be contacted with the molecule before seeding on the set of two adhesive patterns, after seeding on the set of two adhesive patterns or before and after seeding. In addition, in this context, one group of tumor cells is contacted with the molecule and another group is not (control group). Optionally, a further group of tumor cells may be contacted with a molecule known to decrease the invasive potential of the tumor cells (as positive control). Optionally, the tumor cells can be contacted with a combination of molecules or with different molecules (one group of tumor cells by molecule).

The method may further comprise a step of selecting the molecule as efficient for treating the subject if the molecule decreases the invasive potential of the tumor cell from said subject.

Accordingly, the method for assessing the efficiency of a molecule for the treatment of a tumor in a subject comprises contacting the molecule with a tumor cell from the tumor of the subject, determining the invasive potential of the tumor cell treated with the molecule, comparing the determined invasive potential of the tumor cell treated with the molecule with the invasive potential of the untreated tumor cell and selecting the molecule if the invasive potential is decreased.

In another aspect, the present invention also relates to a method for assessing the efficiency of a molecule for the treatment of a tumor in a subject, wherein the method comprises determining the invasive potential of a tumor cell of said patient by the method according to the present invention and selecting a molecule known to be efficient for a tumor cell classified in the same category of invasive potential than the tumor cell of said patient.

Definition

By "Invasive potential" it is intended the ability of cells to invade neighboring or distant tissues.

By "convex envelope" is intended the minimal convex polygon containing the set of two adhesive patterns.

By the "area defined by the convex envelope" is intended the area covered by the zone comprised in the convex envelope.

By "S" is intended to refer to the surface covered by a eukaryotic cell on a support without any constraint (e.g., a cell on a Petri dish, a plastic or a glass coverslip).

By "D" is intended to refer to the diameter of the disk having the said surface S.

By the "distance between the two adhesive patterns" is intended the distance between the two closer points of the two adhesive patterns.

By "about" is intended the value more or less than 5%.

By "doublet" is intended the two cells immobilized on a set of two adhesive patterns.

By "descriptor" is meant a parameter quantifying a feature of the analyzed cell.

BRIEF DESCRIPTION OF THE FIGURES

FIG. 1-FIGS. 1A and 1B present relevant morphological descriptors and a statistical procedure used to discriminate tumor cells for their invasive potential according to the present invention. FIG. 1A. As a structural descriptor, the percentage of highly polarized cells is quantified in individual cells as the relative coordinates of the centrosome from the nucleus center of mass. Miss-polarized centrosomes are removed (grey plots), then the percentage of filtered centrosomes facing junction (black plots) is calculated to the total centrosome population. Further descriptors used according to the present invention are the inter-nuclear distance and the cell-cell connectivity, defined as the difference between the area of the convex envelope (dashed line) surrounding the cell doublet and the area of the cell doublet. Results for descriptors of 13 breast adenocarcinoma with gradual invasive potential are shown. FIG. 1B. Eigenvectors representation of the descriptors, determined from a principal component analysis of the results, displaying the correlation between descriptors according to the invention.

FIG. 2—FIGS. 2A to 2D illustrate results of a study realized according to the present invention. FIG. 2A. Scatterplot of centered data to the mean for each cell line replicate with the eigenvectors overlayed. FIG. 2B. Dendrogram resulting from the study showing the clustering of the 13 cell lines using the three descriptors according to the invention. Each replicate is individually classified. Pearson's correlation, n>300 analyzed cells. FIG. 2C. Scoring of the replicates according to their classification. MCF10A and MDA-MB-231 are arbitrary set as low-invasive (Score=1) and high-invasive (Score=4) references, respectively. FIG. 2D. Subsequent final classification of the 13 cell lines for their invasive potential according to the mean of the replicates score.

FIG. 3—Comparative Data FIG. 3A. Descriptors used in Burute M, et al. ((2017). Dev Cell. 40, 168-184) to assess EMT in MCF10A cells: Percentage of polarized cells, the polarity index, the internuclear distance, and the intercentrosomal distance. FIG. 3B. Dendrogram resulting of the study showing the clustering of the 13 cell lines using the descriptors displayed in Burute M, et al. ((2017). Dev Cell. 40, 168-184). Pearson's correlation, n>300 analyzed cells in triplicates. FIG. 3C. Subsequent classification of the 13 cell lines for their invasive potential.

FIG. 4—Comparative Data FIG. 4A. The percentage of polarized cells and the inter-nuclear distance are quantified according to Burute M, et al. ((2017). Dev Cell. 40, 168-184), and the cell-cell connectivity descriptor is determined as defined in the present invention. FIG. 4B. Resulting dendrogram showing the clustering of the replicates according to this methodology. FIG. 4C. Final classification of the 13 cell lines for their invasive potential according to this methodology. MCF10A and MDA-MB-231 are arbitrary set as low-invasive and high-invasive references respectively.

EXAMPLES

A study involving 13 cell lines with gradual invasive potential was realized in triplicate. For each cell line, the inter-nuclear distance, cell-cell connectivity, and percentage of highly polarized cells were quantified as shown in FIG. 1A and normalized by their respective mean. After a principal component analysis on these values, eigenvectors are represented in FIG. 1B. This representation allows us to visualize the anti-correlation between the "cell-cell-connectivity" and the "percentage of highly polarized cells" descriptors. Moreover, the "internuclear distance" is found not correlated to the other descriptors.

Figure 2B:
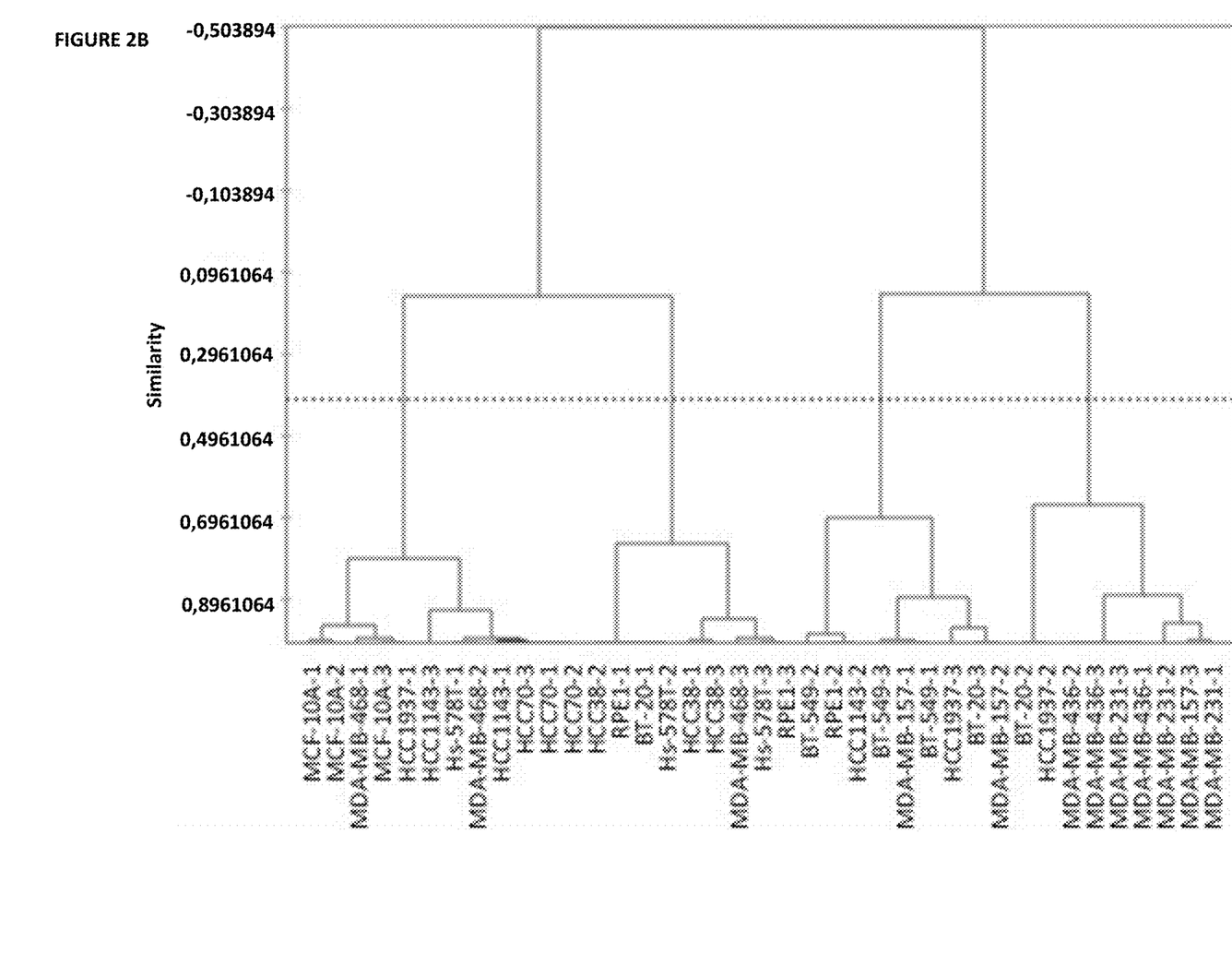
Figure 2C:
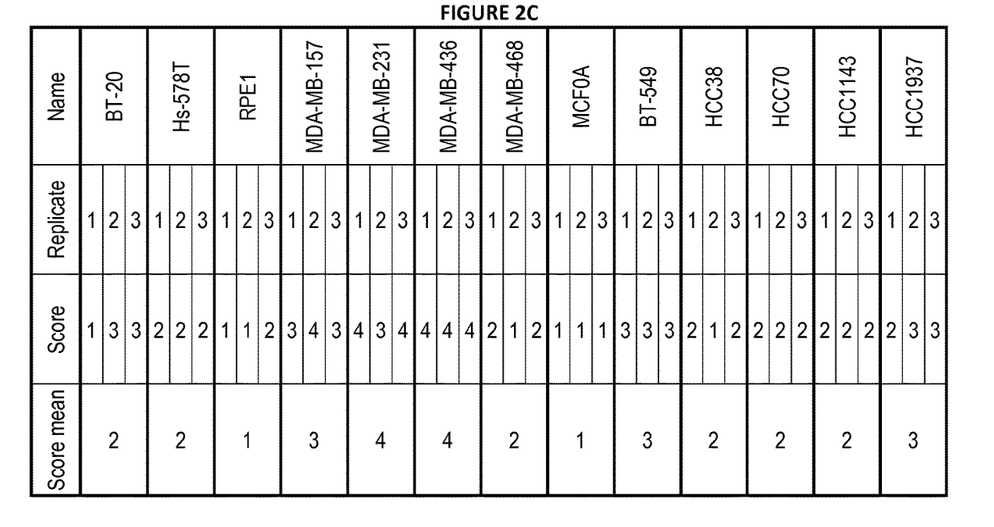
Figure 2D:
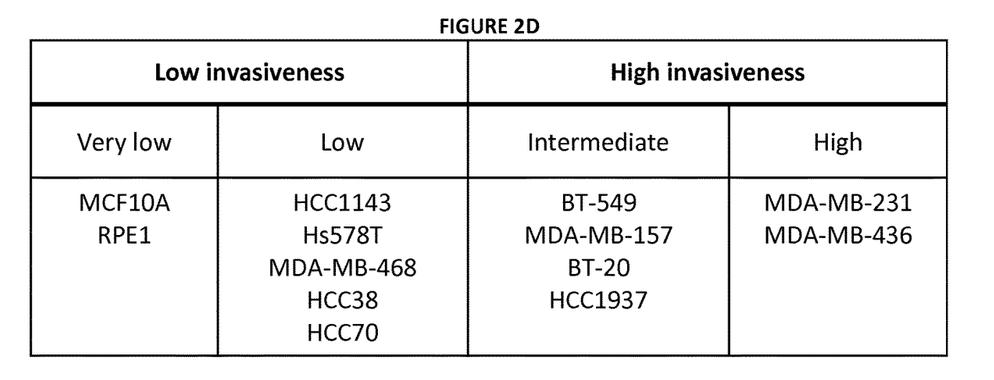

Then, each cell line replicate is individually plotted in the eigenvector representation, as indicated in FIG. 2A. Plot coordinates are then computed using a Pearson's correlation in order to respectively classify each cell line replicate from the others. The resulting dendrogram is shown in FIG. 2B. As a result, two main families, each one encompassing two subfamilies, can accurately be discriminated. Because MCF10A and RPE1 cell lines are known to be non-tumoral, they are used as non-invasive controls. Because MDA-MB-231 is a triple negative breast carcinoma cell line known to be extremely invasive, it is used as a high-invasive control. By scoring cell lines and replicates individually, as shown in FIG. 2C, the mean score allows us to faithfully classify the cell lines within the 4 subfamilies. Based on this classification, the invasive potential of each cell line is determined as shown in FIG. 2D. The overall examination of this classification points out that it was able to cluster non-cancer (MCF10A, RPE1) from the cancer cell lines, and to discriminate low invasive epithelial cells from metastasis (MDA-MB-468) to high-invasive mesenchymal ones (MDA-MB-231, MDA-MB-436, MDA-MB-157). Moreover, the method according to the invention shows a 92% correlation with the histological classification of each cell line, a 84% correlation to their TN BC classification, and a 84% correlation with their Taub et al., signature (Taube et al., 2010, PNAS, 107, 15449-15454). Altogether, these results show that the method according to the invention succeeds in efficiently classifying the 13 breast carcinoma cell lines for their invasive potential.

Figure 3A:
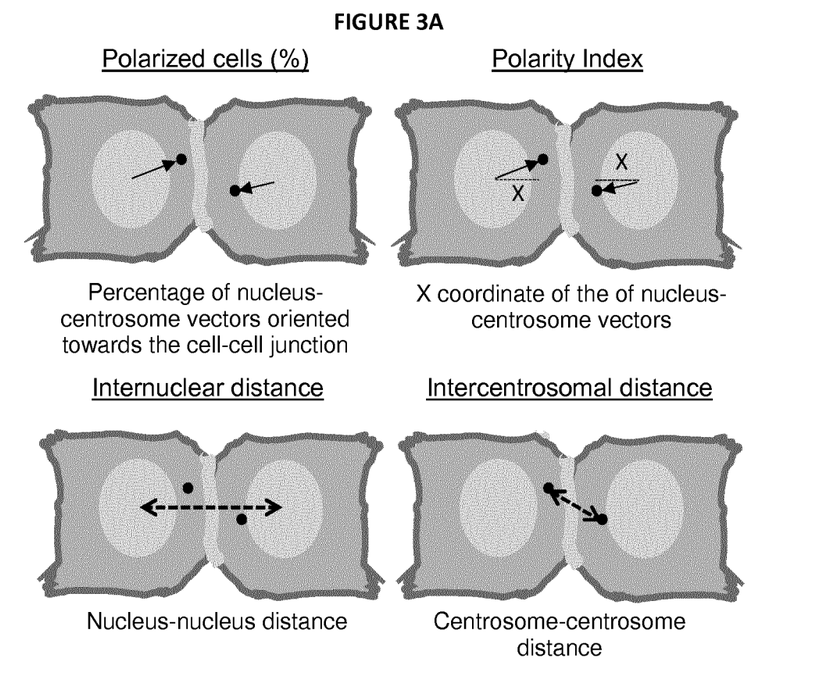
—FIGS. 3A to 3C illustrate the method used in Burute M, et al. ((2017). Dev Cell. 40, 168-184) and why this method is not adapted for classifying tumors by their invasive capacity.
Figure 3B:
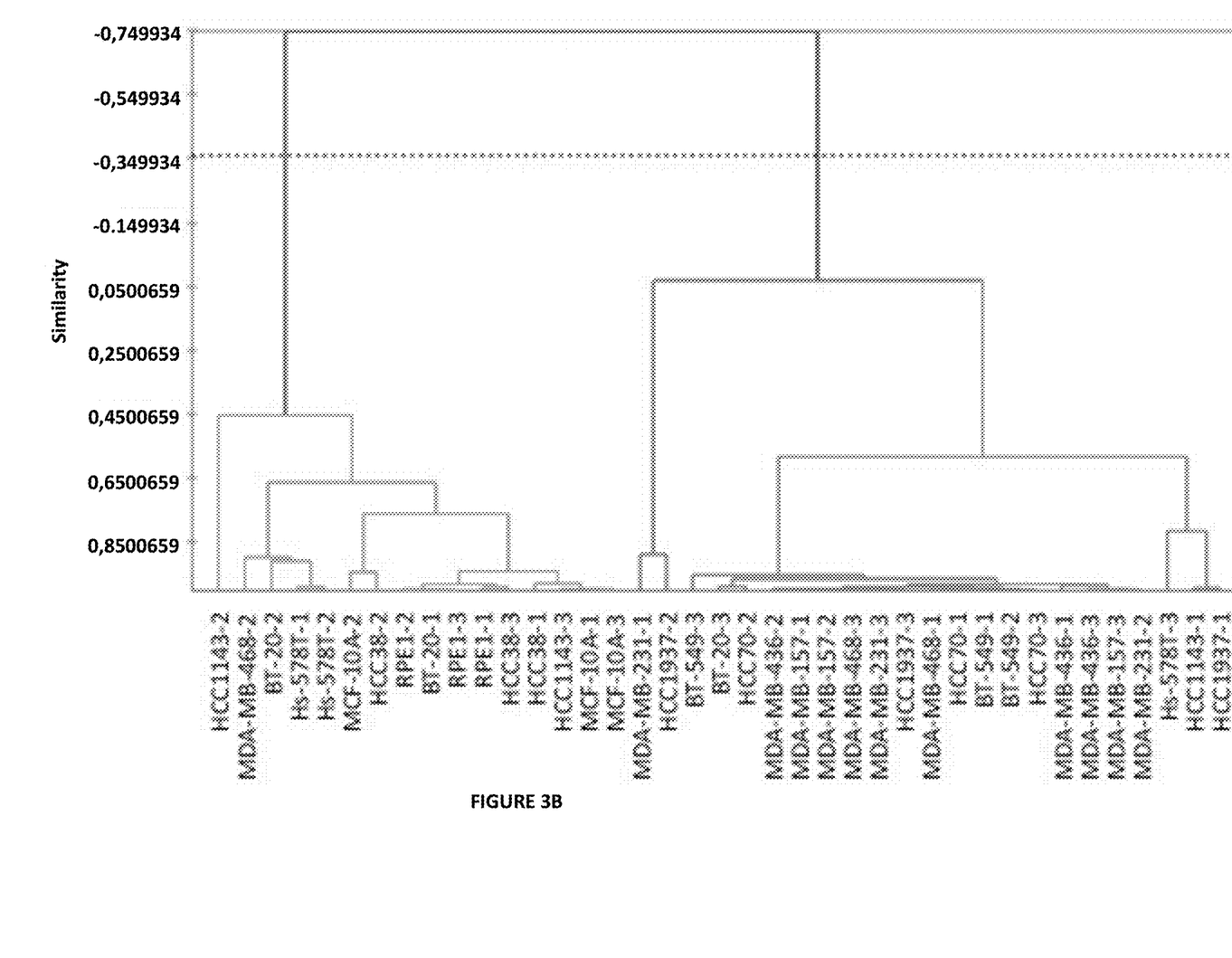
Figure 3C:
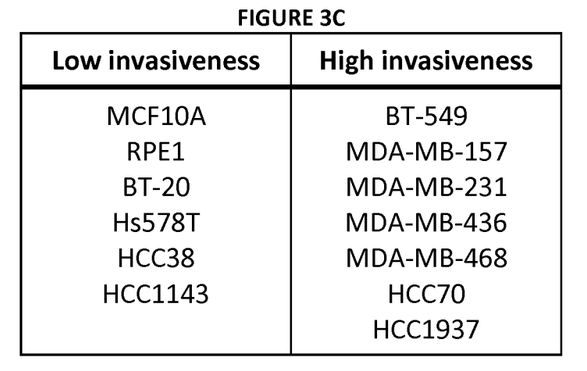

In order to demonstrate that the method employed in Burute M, et al. ((2017). Dev Cell. 40, 168-184) is not suited for finely comparing cancer cells of gradual invasiveness, the inventors directly try to classify the 13 breast carcinoma cell lines by using the descriptors disclosed in this study, as illustrated in FIG. 3A. Results from Pearson's correlation analysis, as shown in FIGS. 3B and 3C, only allow to classify cell lines in 2 families, avoiding a discrimination of cancerous and non-cancerous cells and subsequently failed to relevantly classify the tested cell lines.

Figure 4A:
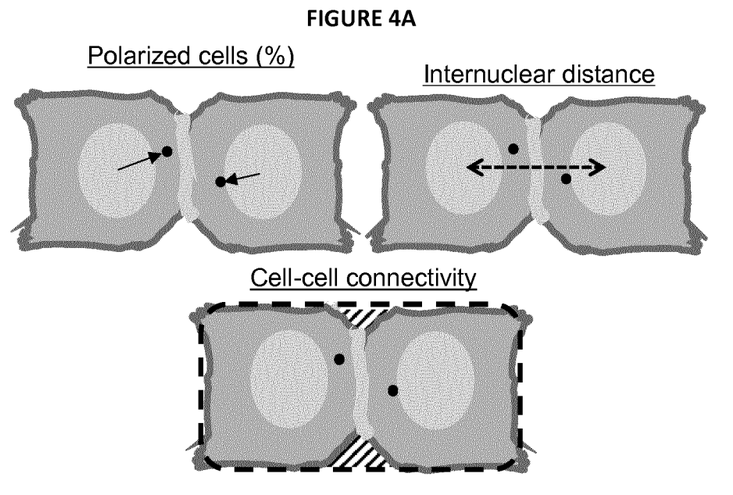
—FIGS. 4A and 4C illustrate the importance of the percentage of highly polarized cells descriptor to efficiently discriminate tumor cells for their invasive potential.
Figure 4B:
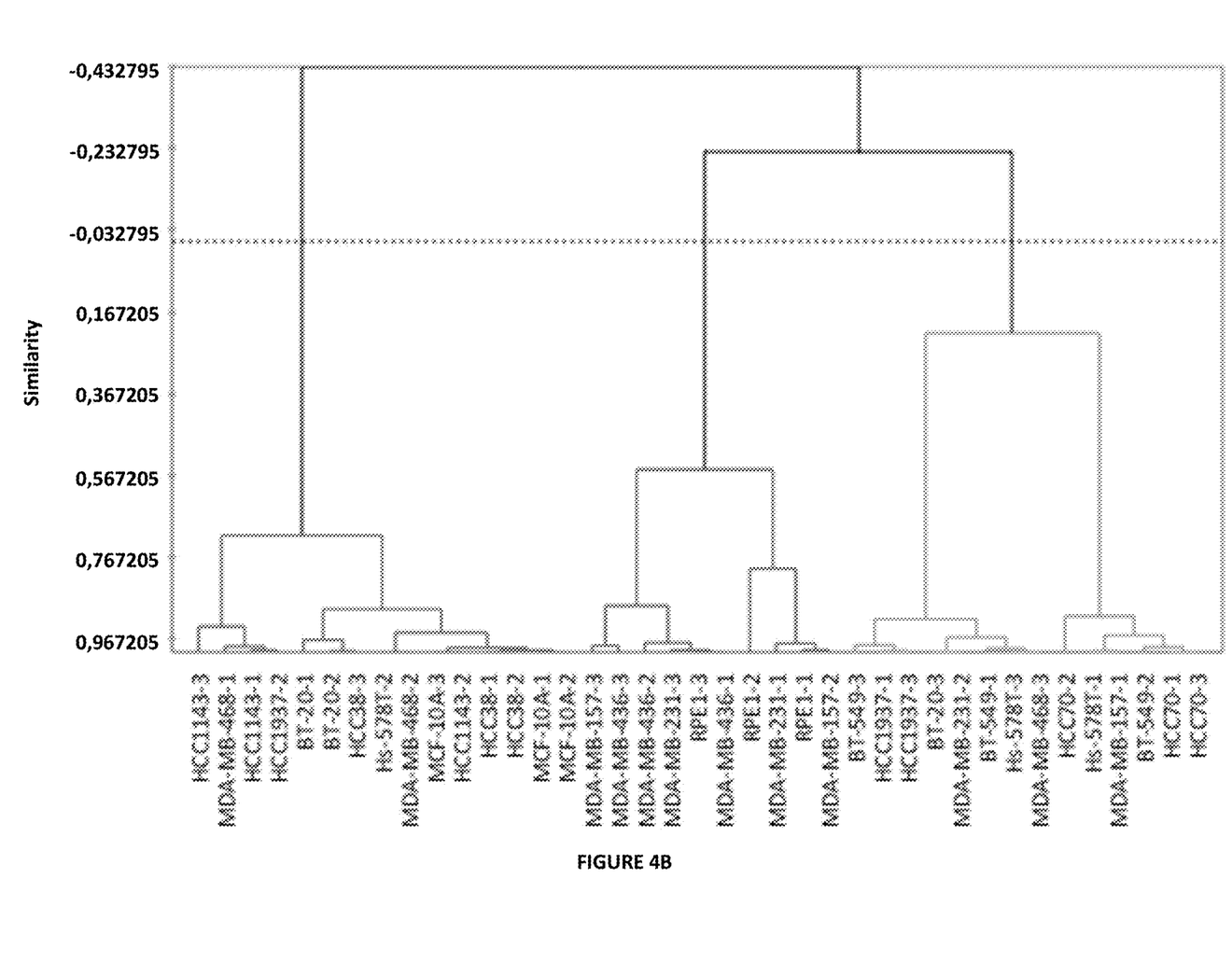
Figure 4C:
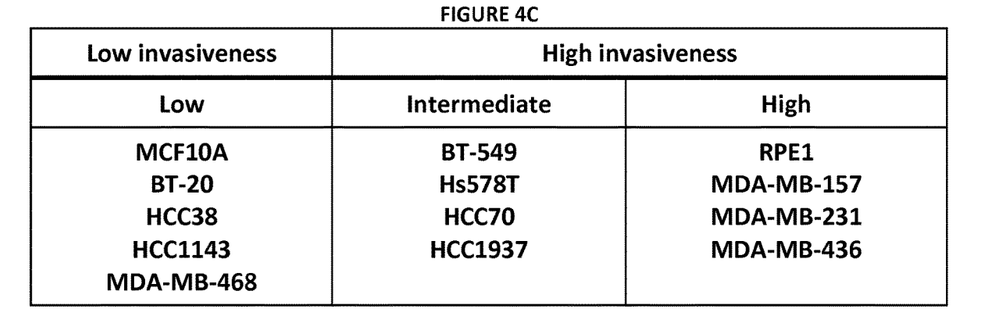

Moreover, to illustrate the importance of the "percentage of highly polarized cells" descriptor to efficiently discriminate tumor cells for their invasive potential, the inventors have retested the methodology according to the invention by substituting said descriptor by the "percentage of polarized cells" one, quantified according to Burute M, et al. ((2017). Dev Cell. 40, 168-184), as illustrated in FIG. 4A. Scatterplot and resulting dendrogram from Pearson's correlation, displayed in FIG. 4B, allow us to cluster the 13 breast carcinoma cell lines in three families. However, regarding final FIG. 4C classification, because it failed to cluster non-cancer (MCF10A, RPE1) from cancer cells, and because a non-cancer (RPE1) and a metastatic highly invasive cell line (MDA-MB-231) are classified together, this methodology unsuccessfully discriminates cells for their invasive potential.

Altogether, these results show that only the methodology according to the invention is able to efficiently classify the 13 breast carcinoma cell lines for their invasive potential.

Materials and Methods

Cell Culture

BT20, Hs578T, RPE1, MDA-MB-157, MDA-MB-231, MDA-MB-436 and MDA-MB-468 cell lines were cultured in Dulbecco's Modified Eagle Medium (Gibco) supplemented with 10% FBS (biowest) and 1% antibiotic-antimycotic (Gibco). BT-549, HCC38, HCC70, HCC1143, HCC1937 were cultured in RPMI 1640 (Gibco) with 10% FBS and 1% antibiotic-antimycotic. MCF10A were cultured in MEGM growth medium (Lonza) according to ATCC protocol.

Cell Micropatterning

Cell-adhesive patterns were achieved from CYTOO (see Worldwide Website: cytoo.com), as H 1100 $\mu m^2$, in 20 $mm^2$ chip format. Cells were seeded at a density of 500,000 cells per chips in culture medium for 24 hours incubation.

Immunostaining

Cells were fixed using cold methanol (−20° C.) during 10 minutes and after a 3 time PBS (Euromedex) washing step, an immunostaining was performed using 0.2% triton X100 (Sigma) for 15 minutes, 3% BSA (Sigma) for 10 minutes. Pericentrin targeting primary antibody (Abcam) was added during 45 minutes in 3% BSA and then a goat anti-rabbit Alexa488 secondary antibodies (LifeTech) during 30 minutes. After 3 PBS wash, chips were mounted on microscope slides using ProLong Gold antifade reagent with DAPI (LifeTech).

Image Acquisition

Images were acquired using an Eclipse-Ti spinning disk microscope with a 40× objective (Nikon). Acquisitions were automatically achieved using homemade journals written in MetaMorph software (Molecular Devices).

Image Processing

Image processing was performed using an ImageJ (NIH) macro. First fluorescent cell-adhesive patterns were individualized using a template matching method. Second, nucleus and centrosome detection were realized based on thresholding and size filtering within each cell of the doublet. Taking into account that only cell doublets were considered for further analysis, groups of cells encompassing two nuclei and two centrosomes were exclusively retained. Nucleus center of mass was computed and each centrosome is assigned to the closest nucleus. Third, the nucleus-centrosome and nucleus-nucleus vectors were computed.

Then a post-processing step was realized in order to quantify the orientation and connectivity of each cell within a doublet.

The inter-nuclear distance was measured as the length of the nucleus-nucleus vector.

The cell-cell connectivity was defined as the difference between the area of the convex envelope surrounding the cell doublet and the area of the cell doublet.

The percentage of highly polarized cells to the total population was quantified as the relative coordinates of the centrosome from its nucleus in the nucleus-nucleus axis of reference where the maximum radius of the nucleus was the arbitrary unit. Highly polarized cells were then defined as cells having a centrosome located in close proximity of the cell-cell junction, in a triangular area defined as:

$$|y| \le (x-0.5)*\tan 60$$

with $0.5 \le x \le 2$

Statistical Analysis

In order to increase the relevance of the measures, the structural descriptors were weighted using a statistical procedure named principal component analysis, and computed using XLSTAT software.

The invention claimed is:

1. A method for predicting the invasive potential of a tumor cell, comprising:
    providing a culture device comprising a planar substrate and at least ten sets of two adhesive patterns for culturing adherent cells on said substrate, wherein the two adhesive patterns are sufficiently separated from each other by an essentially non-adhesive intercalating area for preventing a cell on a first adhesive pattern to reach another adhesive pattern; and, the area covered by the two adhesive patterns and the intercalating area is sufficient to adhere two animal cells, and wherein each set of two adhesive patterns is isolated by a cytophobic surrounding region;
    seeding at least one tumor cell on said sets of two adhesive patterns;
    culturing said tumor cell so as to obtain one cell doublet from one cell division on said sets of two adhesive patterns;
    measuring at least three parameters on said sets of two adhesive patterns for said tumor cell, said at least three parameters comprising:
        the internuclear distance for each set of two adhesive patterns, which is the length between the nucleus of two cells in the doublet on each set of two adhesive patterns;
        the cell-cell connectivity for each set of two adhesive patterns; which is the difference between the area of the convex envelope surrounding the cell doublet and the area of the cell doublet;
        and
        the percentage of highly polarized cells to the total cell population on said sets of two adhesive patterns, wherein the highly polarized cells are cells having a centrosome located in close proximity of the cell-cell junction, in a triangular area defined as:

$$|y| \le (x-0.5)*\tan 60$$

with $0.5 \le x \le 2$ wherein x is the position of the centrosome on a nucleus-nucleus axis pointing toward the intercellular junction and y is the position of the centrosome on an axis perpendicular to the nucleus-nucleus axis, the unit being the radius of the nucleus;
    the percentage of highly polarized cells is the ratio of the number of cells having a high polarization as defined above by the total number of cells*100; and
    determining the tumor cell invasive potential based on the at least three measured parameters for the at least 10 cell doublets, by comparison with reference cells with a predetermined invasive potential, by performing statistical analysis.

2. The method of claim 1, wherein the distance between the two adhesive patterns is comprised between about 2/3 D and about 4/3 D, D being the diameter of a disk having the surface S covered by the cell on a support without any constraint, and the area covered by the adhesive pattern for each cell is less than 80% of the cell surface S covered by the cell on a support without any constraint.

3. The method of claim 1, wherein the set of two adhesive patterns has the form of a H.

4. The method of claim 1, wherein, in addition to the tested tumor cell, cells of reference with predetermined invasive potential are seeded on the device, cultured and the parameters are measured.

5. The method of claim 4, wherein said cells of reference with predetermined invasive potential are selected from the group consisting of a cell with very low or no invasive potential, a cell with low invasive potential, a cell with intermediate invasive potential, a cell with high invasive potential and a cell with very high invasive potential, according to the Nottingham Histologic Score system or the WHO/IARC classification.

6. The method of claim 5, wherein:
    four types of reference cells with predetermined invasive potential are used in the method and are a cell with very low or no invasive potential, a cell with low invasive potential, a cell with intermediate invasive potential, a cell with high invasive potential and a cell with very high invasive potential, according to the Nottingham Histologic Score system or the WHO/IARC classification,
    the culture device comprising a plane substrate having at least 50 sets of two adhesive patterns per cell type, whereby 50 cell doublets per cell type are used, and
    the invasiveness potential of the tested cells are determined by statistical analysis carried out so as to determine the reference cells having the highest similarity with the tested cells.

7. The method of claim 6, wherein the statistical analysis is carried out by principal component analysis.

8. The method of claim 1, wherein the tumor is a solid tumor.

9. The method of claim 8, wherein the solid tumor is a carcinoma.

10. The method of claim 1, wherein the tumor is selected from the group consisting of breast cancer, colorectal cancer, lung cancer, kidney cancer, thyroid cancer, prostate cancer, liver cancer, pancreas cancer, head and neck cancer, and ovaries cancer.

11. A method for providing information useful for diagnostic or prognosis of a subject comprising performing the method according to claim 1, thereby determining the invasive potential of the tumor cell from the subject.

12. A method for assessing the efficiency of a molecule for the treatment of a tumor in a subject comprising contacting the molecule with a tumor cell from the tumor of the subject, determining the invasive potential of the tumor cell treated with the molecule, comparing the determined invasive potential of the tumor cell treated with the molecule with the invasive potential of the untreated tumor cell and selecting the molecule if the invasive potential is decreased, wherein the invasive potential of the tumor cell is determined by the method according to claim 1.

13. The method of claim 6, wherein:
the reference cells with no or very low invasive potential are selected from a non-tumor cell,
the reference cells with low invasive potential are selected from the group consisting of HCC1143, Hs578T, MDA-MB-468, HCC38, HCC70,
the reference cells with intermediate invasive potential are selected from the group consisting of BT-549, MDA-MB-157, BT-20, and HCC1937, and
the reference cells with high invasive potential are selected from the group consisting of MDA-MB-231 and MDA-MB-436.

14. The method according to claim 7, wherein the statistical analysis leads to the determination of a score enabling the classification of the tumour cell into one of the following four categories 1) no or very low invasive potential, 2) low invasive potential, 3) intermediate invasive potential, and 4) high invasive potential.

* * * * *